United States Patent
Wu et al.

(10) Patent No.: US 11,986,400 B2
(45) Date of Patent: May 21, 2024

(54) MAGNETIC IMPACTOR ASSEMBLY

(71) Applicant: THINK SURGICAL, INC., Fremont, CA (US)

(72) Inventors: Jonathan Wu, Fremont, CA (US); Mark Dixon, Fremont, CA (US)

(73) Assignee: Think Surgical, Inc., Fremont, CA (US)

( * ) Notice: Subject to any disclaimer, the term of this patent is extended or adjusted under 35 U.S.C. 154(b) by 375 days.

(21) Appl. No.: 16/348,735

(22) PCT Filed: Nov. 6, 2017

(86) PCT No.: PCT/US2017/060145
§ 371 (c)(1),
(2) Date: May 9, 2019

(87) PCT Pub. No.: WO2018/089334
PCT Pub. Date: May 17, 2018

(65) Prior Publication Data
US 2019/0290449 A1   Sep. 26, 2019

Related U.S. Application Data

(60) Provisional application No. 62/420,064, filed on Nov. 10, 2016.

(51) Int. Cl.
*A61B 90/50*   (2016.01)
*A61B 34/00*   (2016.01)
(Continued)

(52) U.S. Cl.
CPC ............ *A61F 2/4609* (2013.01); *A61B 34/30* (2016.02); *A61B 34/73* (2016.02); *A61B 90/50* (2016.02);
(Continued)

(58) Field of Classification Search
CPC ...................................................... A61F 2/4609
See application file for complete search history.

(56) References Cited

U.S. PATENT DOCUMENTS 2,570,625 A * 10/1951 Zimmerman ........ A63H 33/046
446/92
4,865,324 A * 9/1989 Nesis .................... A63F 9/0811
273/155

(Continued)

FOREIGN PATENT DOCUMENTS

| JP | 2009525079 A | 7/2009 |
| WO | 2011041439 A2 | 4/2011 |
| WO | 2014091454 A1 | 6/2014 |

OTHER PUBLICATIONS

Supplementary EU Search Report issued in EP17869499, dated Jun. 9, 2020.
(Continued)

*Primary Examiner* — Zade Coley
(74) *Attorney, Agent, or Firm* — MaxGoLaw PLLC

(57) ABSTRACT

A magnetic impactor assembly is described herein. The magnetic impactor assembly generally includes a guide receptacle, and an impactor guide magnetically coupled to the guide receptacle to form a magnetic interface therebetween. The guide receptacle is attachable to a surgical device such as a surgical robotic manipulator arm. The impactor guide receives and guides an impactor to permit a user to impact a prosthesis into a bone of a patient in a planned position and orientation. The magnetic impactor assembly reduces the transmission of excessive forces to a patient or the surgical device if an off-axis impaction force is generated on the impactor through the decoupling of the impactor guide from the guide receptacle.

17 Claims, 11 Drawing Sheets

(51) Int. Cl.
  *A61B 34/30* (2016.01)
  *A61F 2/46* (2006.01)
  *A61B 90/57* (2016.01)
  *A61F 2/30* (2006.01)

(52) U.S. Cl.
  CPC ... *A61B 2090/508* (2016.02); *A61B 2090/571* (2016.02); *A61F 2002/30079* (2013.01); *A61F 2002/4687* (2013.01)

(56) References Cited

U.S. PATENT DOCUMENTS

| | | | |
|---|---|---|---|
| 5,347,253 A * | 9/1994 | Ogikubo | A63F 9/12 273/239 |
| 5,553,198 A | 9/1996 | Wang et al. | |
| 8,486,084 B2 | 7/2013 | Huene | |
| 2003/0028196 A1 * | 2/2003 | Bonutti | A61B 17/1764 606/87 |
| 2004/0153080 A1 | 8/2004 | Dong et al. | |
| 2009/0222017 A1 | 9/2009 | Lye | |
| 2013/0096563 A1 | 4/2013 | Meade et al. | |
| 2013/0218166 A1 * | 8/2013 | Elmore | A61B 90/06 606/104 |
| 2013/0296872 A1 * | 11/2013 | Davison | G06F 30/20 606/87 |
| 2014/0180296 A1 | 6/2014 | Gillman et al. | |
| 2014/0303631 A1 * | 10/2014 | Thornberry | A61F 2/4609 606/91 |
| 2015/0065007 A1 * | 3/2015 | Klepper | A63H 33/046 446/92 |
| 2015/0100060 A1 | 4/2015 | Black | |
| 2015/0283475 A1 * | 10/2015 | Hiller | A63H 33/046 446/92 |
| 2015/0313722 A1 * | 11/2015 | Hudak, Jr. | A61F 2/4609 606/99 |
| 2016/0202134 A1 | 7/2016 | Malackowski et al. | |

OTHER PUBLICATIONS

Reasons for Rejection issued in corresponding Japanese Patent Appln. No. 2019-515309, dated Sep. 21, 2021.

* cited by examiner

MAGNETIC IMPACTOR ASSEMBLY

RELATED APPLICATIONS

This application claims priority benefit of U.S. Provisional application Ser. No. 62/420,064 filed Nov. 10, 2016; the contents of which are hereby incorporated by reference.

TECHNICAL FIELD

The present invention generally relates to the field of orthopedic surgery, and more particularly to compliant interfaces that reduce excessive or off-axis impaction forces generated on a subject's anatomy or a surgical device while performing orthopedic procedures.

BACKGROUND

Total joint arthroplasty (TJR) involves the replacement of a subject's joint with prosthetic components. In particular, total hip arthroplasty (THA) requires the implantation of both a femoral prosthesis and an acetabular prosthesis. Traditionally, a surgeon pre-operatively plans the position and orientation (POSE) of the prosthesis in the bone before the bone is prepared and the prosthesis is seated or implanted. The surgeon then uses manual instruments to prepare the bones to receive the implants in the planned POSE. Unfortunately, the use of manual instrumentation can be unpredictable as being subject to the skill of the particular surgeon. Therefore, to improve the implant procedures, computer-assisted surgical systems have become popular to prepare and implant the cup prosthesis more accurately.

One such surgical system for planning and executing a THA procedure is the TSolution One® Surgical System (THINK Surgical, Inc., Fremont, CA). The TSolution One® includes a pre-operative planning workstation for generating a surgical plan and a robotic surgical device to execute the pre-operative plan intra-operatively. Prior to the procedure, the surgeon pre-operatively plans a desired POSE for the femoral and cup prosthesis using three-dimensional (3-D) bone models of the patient's anatomy and computer-aid design (CAD) files of the prostheses. The plan is then transferred to the robotic device in the operating room (OR). Intra-operatively, the cup portion of the THA procedure starts by fixating the robotic device to the anatomy by the use of pins that are screwed into the bone of a patient. After the fixation step, the bone is registered to the robotic device, which transforms the position of the bone and the coordinates of the surgical plan into the robotic coordinate system. The robotic device then positions and constrains a reamer, by way of physical guide attached to the electro-mechanical arm, in the planned POSE to permit the surgeon to prepare the acetabulum. Following the preparation of the acetabulum, an impactor with the cup prosthesis is attached to the electro-mechanical arm. The arm guides and constrains the impactor in the planned POSE while the surgeon applies a series of impaction forces on the impactor to implant the cup prosthesis.

However, during impaction, if the surgeon exerts a force on the impactor that is off-axis from the longitudinal axis of the impactor (i.e., the impaction axis), the off-axis forces get transmitted to the mechanical arm. The off-axis forces may cause damage to the components of the mechanical arm resulting in the need to replace the arms components or, at the very least, re-calibrate the accuracy of the arm. In this case, the surgeon may have to complete the procedure with less-accurate manual instrumentation, which may additionally increase the overall operating time. Furthermore, the excessive forces may not only damage the surgical device, but the pelvis may be more susceptible to movement, which may negatively affect the final prosthesis anteversion/inclination angles.

In addition to impaction forces that may inadvertently damage a surgical device, there are other situations where it may be beneficial to reduce excessive forces transmitted to a patient's anatomy. One particular situation in which a patient's anatomy is subjected to excessive forces is during the removal of primary prostheses in revision TJR. Traditionally, to remove the prostheses, a surgeon assembles a slap hammer thereto, and applies a series of impaction forces directed away from the prosthesis. However, it is not uncommon for the surgeon to rip out or damage the bone while applying these impaction forces. The damaged bone may cause patient complications and/or require additional treatment to fix the damage.

Therefore, there is a need in the art for a device and mechanism that reduces the transmission of off-axis or excessive impact forces received by a surgical device during the impaction of an implant in a bone. There is a further need to control an amount of force generated on a patient during implant removal.

SUMMARY

A guide assembly for an impactor includes an impactor guide having a frame and one or more guide magnetic regions assembled laterally to the frame. The frame includes an opening to support and translationally guide the impactor along an impaction axis concentric to the opening. The guide assembly further includes a guide receptacle having a bracket connected to a top support, and one or more receptacle magnetic regions complementary to the one or more guide magnetic regions. The guide receptacle receives the impactor guide and forms a magnetic interface between the one or more receptacle magnetic regions complementary to the one or more guide magnetic regions. One of the impactor guide or guide receptacle at least partially breaks from the magnetic interface when an off-axis impaction force is applied to the impactor.

A guide assembly for an impactor includes an impactor guide having a frame and an opening to support and translationally guide an inserted impactor along an impaction axis concentric to the opening, and at least a first magnetic region and a second magnetic region on opposing ends of the frame. The guide assembly further includes a guide receptacle for receiving the impactor guide, the guide receptacle having at least a third magnetic region and a fourth magnetic region, wherein the third magnetic region and fourth magnetic region magnetically couple with the first magnetic region and the second magnetic region, respectively, to form a magnetic interface. One of the impactor guide or guide receptacle at least partially breaks from the magnetic interface when an off-axis impaction force is applied to the impactor.

A magnetic impactor assembly includes a magnetic impactor receptacle having a first magnetic region and a magnetic impactor guide having a second magnetic region removably coupled to the first magnetic region to form a magnetic interface. The magnetic impactor assembly further includes an impactor having an impaction axis, where the impactor is operably associated with the magnetic impactor guide. A prosthesis is removably attached to an end of the impactor. One of the impactor receptacle or impactor guide decouples from the magnetic interface when either: i. a pre-determined impaction force applied to the impactor is exceeded; or ii. an impaction force deviating from the impaction axis is applied to the impactor.

BRIEF DESCRIPTION OF THE DRAWINGS

Examples illustrative of embodiments are described below with reference to the figures attached hereto. In the figures, identical structures, elements or parts that appear in more than one figure are generally labeled with a same numeral in all the figures in which they appear. Dimensions of components and features shown in the figures are generally chosen for convenience and clarity of presentation and are not necessarily shown to scale. The figures are listed below.

DETAILED DESCRIPTION

Figure 1A:
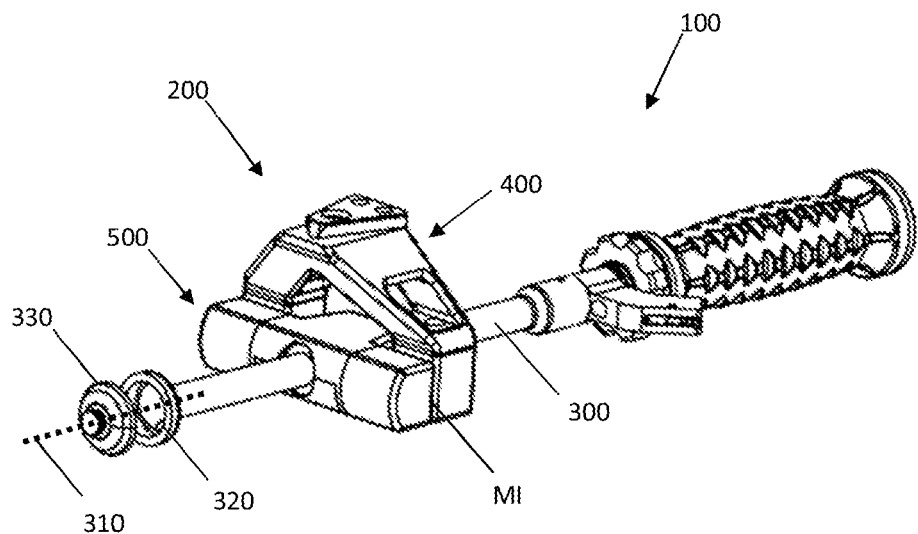
FIG. 1A depicts an impactor assembly in accordance with embodiments of the invention.

The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment may be deleted from that embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

Definitions

Unless indicated otherwise, explicitly or by context, the following terms are used herein as set forth below.

As used in the description of the invention and the appended claims, the singular forms "a," "an" and "the" are intended to include the plural forms as well, unless the context clearly indicates otherwise.

Also, as used herein, "and/or" refers to and encompasses any and all possible combinations of one or more of the associated listed items, as well as the lack of combinations when interpreted in the alternative ("or").

As used herein, the term "impactor" refers to any object which receives a force or produces an impact event. Although the scope of this technology is not limited to these examples, an "impactor" can include an instrument for implanting a prosthetic as described in U.S. Pat. No. 7,335,207, an orthopedic impacting tool for striking an object in U.S. Pat. No. 8,393,409, a sliding weight of a slap hammer as described in U.S. Pat. No. 8,486,084, and similar impaction devices that may receive a force or produce an impact event.

As used herein, the term "impaction axis" generally refers to a center axis extending from a first end to a second end of an impactor.

As used herein, the term "off-axis" refers to any direction which is not substantially parallel or substantially anti-parallel to the impaction axis.

Disclosed herein is the use of "magnets", which is to refer to any material or object that generates a magnetic field.

As used herein, the terms "first", "second", "third", etc., do not necessarily refer to a consecutive order of elements, but may rather denote the difference between like elements associated with other components.

The present invention has utility as a device and mechanism for reducing the transmission of off-axis or excessive impact forces to a surgical device or a patient's anatomy during the implantation or removal of a prosthesis in a bone. As reference is made herein to total hip arthroplasty (THA) as an applicable procedure, it should be understood that embodiments of the present invention may be readily applied to procedures involving other bones or joints found within the body. These other joints illustratively include the knee joint, shoulder joint, ankle joint, wrist joint, finger joint, toe joint, or other joints. It should also be appreciated that the embodiments described herein are applicable to industries outside of the medical field where it is desirable to reduce the transmission and/or control an amount of force exerted on an object of interest.

Embodiments of the present invention generally provide a magnetic guide assembly. The magnetic guide assembly is particularly advantageous for reducing the transmission of off-axis impaction forces to a robotic arm during the impaction of the acetabular cup in THA. This is accomplished through the use of a magnetic interface as further described below. The detent used in this device has been advantageously determined to be magnetically operated although it will be apparent that other mechanisms may be employed.

In a particular embodiment, and referring now to FIG. 1A, an impactor assembly 100 generally includes a guide assembly 200 and an impactor 300. The guide assembly 200 includes a guide receptacle 400 and an impactor guide 500. The guide receptacle 400 is configured to receive and magnetically couple with the impactor guide 500 to form a magnetic interface MI. The impactor guide 500 is further configured to hold and guide the impactor 300 during impaction.

The impactor 300 has an impaction axis 310 and is operably associated within the impactor guide 500 such that a user can translate the impactor 300 along the impaction axis 310 and rotate the impactor 300 about the impaction axis 310. In a particular embodiment, the impactor 300 includes a prosthesis attachment member 320 configured to removably attach a prosthesis 330 thereto. The prosthesis 330 may be an acetabular cup component for THA, but it should be appreciated that other prostheses for replacing a portion of a subject's anatomy is also feasible. The prosthesis attachment member 320 may be any mechanism capable of removably attaching the prosthesis including a threaded shaft, a non-threaded shaft, a clamp, a projection having a unique shape that mates with a corresponding shape associated with a portion of the prosthesis 330, or equivalents thereof.

Figure 1B:
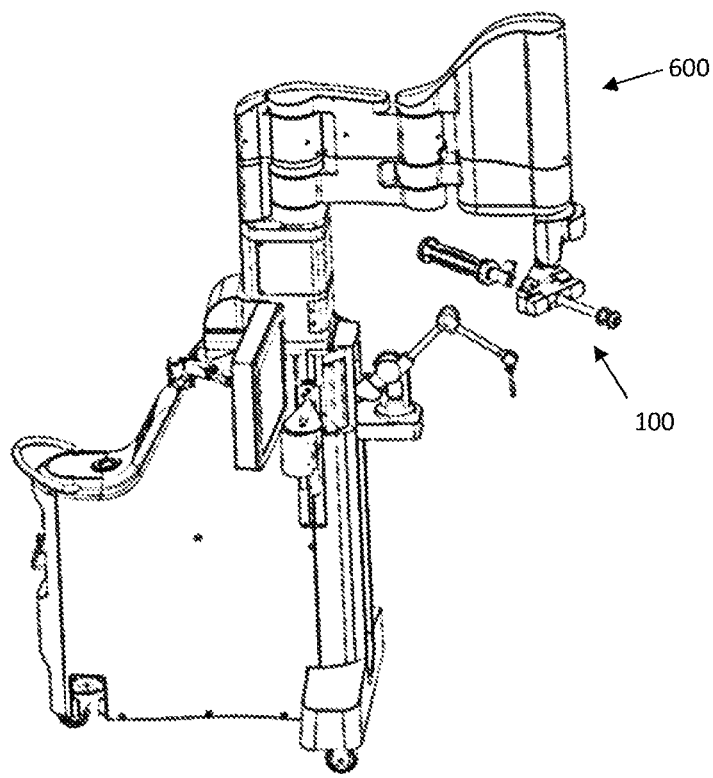
FIG. 1B depicts an impactor assembly coupled to a surgical device in accordance with embodiments of the invention.

In a specific embodiment, the guide receptacle 400 is further configured to removably couple with a computer-assisted surgical system, where the guide assembly 200 and surgical system constrains the movement of the impactor 300 to a planned POSE during impaction (except for the translational motion along the impaction axis 310 and rotational motion about the impaction axis 310). For example, with reference to FIG. 1B, the magnetic impactor assembly 100 is coupled to an electro-mechanical arm 600 of a robotic surgical system. Examples of robotic surgical systems capable of guiding the impactor 300 to a planned POSE are described in U.S. Pat. Nos. 5,086,401, 8,498,744 and U.S. Pat. App. No. 20140039681. However, it should be appreciated that the scope of the present invention does not require all components shown in FIG. 1B to be present or used when present, nor is the scope limited to these components.

Figure 1C:
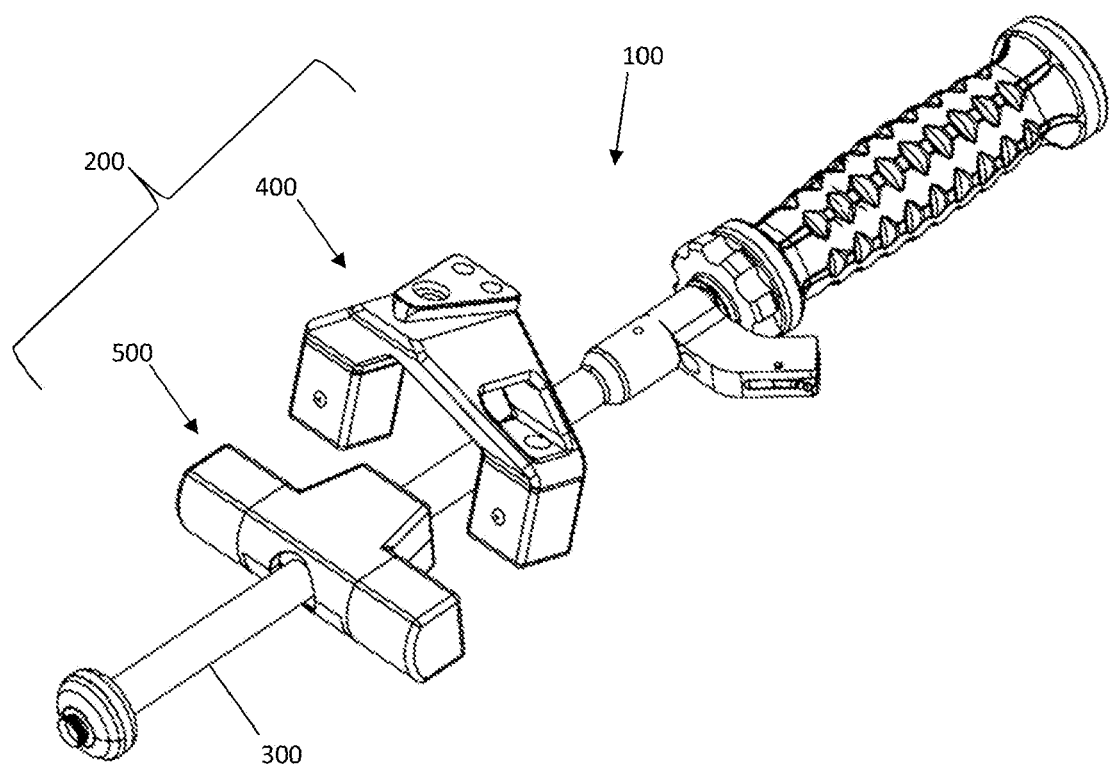
FIG. 1C illustrates how an impactor may be detached from a surgical device in accordance with embodiments of the invention.

The impactor assembly 100 generally functions as follows. During the impaction of a prosthesis 330, a user applies a series of forces to one end of the impactor 300. With reference to FIG. 1C, if the impaction force received on the impactor 300 is off-axis from the impaction axis 310 (shown in FIG. 1A), the impactor guide 500 decouples from the guide receptacle 400 breaking the magnetic interface MI. This effectively reduces the transmission of any off-axis impaction forces that would otherwise be transmitted to an external device (e.g., electro-mechanical arm 600) that rigidly holds, guides, and/or constrains the impactor 300. Specific embodiments of the elements and components of the guide assembly 200 are further described below.

Figure 2A:
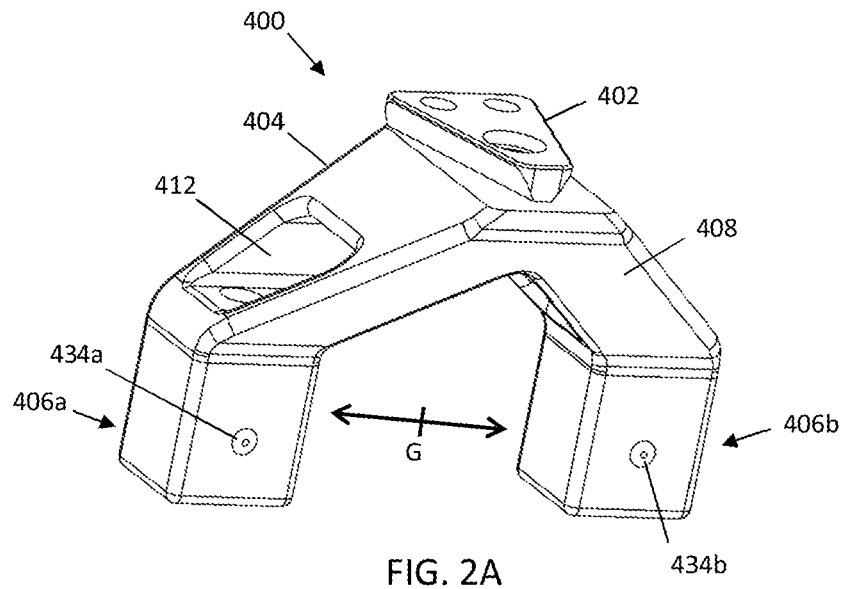
FIG. 2A depicts a guide receptacle in accordance with embodiments of the invention.

With reference to FIG. 2A, a particular embodiment of the guide receptacle 400 includes a bracket 402, a top support 404, and at least one receptacle magnetic region 406. In specific embodiments, the guide receptacle 400 includes two receptacle magnetic regions (406a, 406b) separated by a gap G. It should be appreciated however that embodiments of the invention may include only one magnetic region and still be operable and useful. The bracket 402 is attached to the top support 404 and is configured to couple the guide receptacle 400 to a surgical device or instrument, illustratively including the electro-mechanical arm 600. The bracket 402 may couple the guide receptacle 400 to the surgical device using fastening elements (e.g., screws, latches, and couplings), adhesives, magnets, and the like. In a particular embodiment, the bracket 403 is shaped in the form of a male dove-tail joint as described in U.S. Prov. Pat. App. No. 62/433,373. The top support 404 supports the magnetic region(s) (406a, 406b), facilitates the assembly of the components of the guide receptacle 400, and/or provides a link between the magnetic region(s) (406a, 406b) and the bracket 402. In a specific embodiment, the top support 404 may include a plurality of openings 412, to reduce the overall weight of the guide receptacle 400.

Figure 4A:
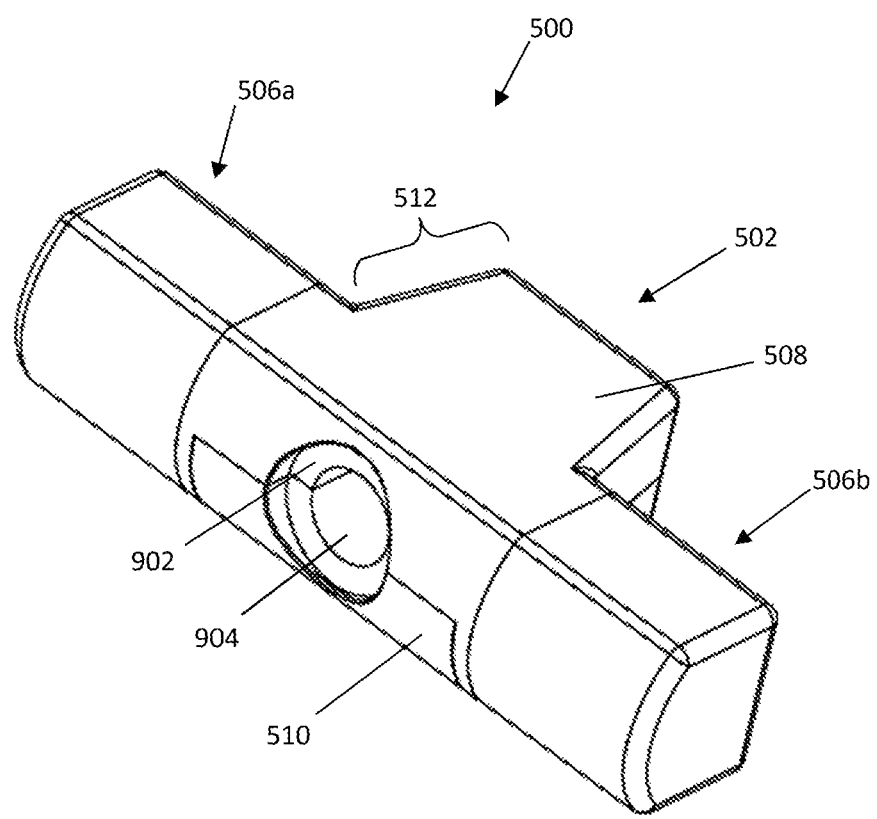
FIG. 4A depicts an impactor guide in accordance with embodiments of the invention.

The receptacle magnetic regions (406a, 406b) are configured to produce magnetic fields to facilitate the magnetic coupling of the receptacle magnetic regions with one or more guide magnetic regions (506a, 506b) (as shown in FIG. 4A) associated with the impactor guide 500. The production of the magnetic fields may be accomplished in several different ways. In a particular embodiment, each magnetic region (406a, 406b, 506a, 506b) is a single solid body made entirely of a magnetic material. In other embodiments, each magnetic region (406a, 406b, 506a, 506b) is at least a partial solid body where only a portion of the body is made of a magnetic material, such as a single surface or wall of the body. In some embodiments, each magnetic region (406a, 406b, 506a, 506b) is a single body that is coated with a magnetic material. In another embodiment, each magnetic region (406a, 406b, 506a, 506b) is made of a magnetizable material having a conductive coil wrapped there around to induce and/or control a magnetic field by flowing current through the coil. Other embodiments for producing the magnetic fields are further described below.

Figure 2B:
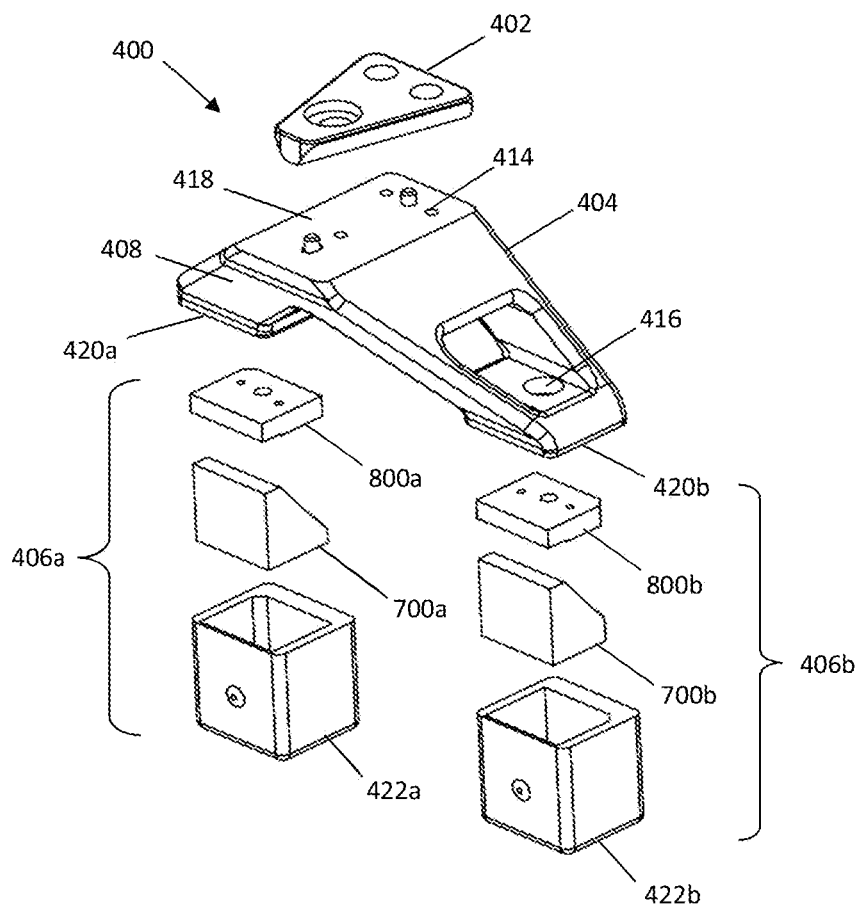
FIG. 2B depicts an exploded view of a guide receptacle in accordance with embodiments of the invention.

With reference to FIGS. 2A and 2B, a specific embodiment of components associated with the guide receptacle 400 is shown, where FIG. 2A is an assembled view of the guide receptacle 400, and FIG. 2B is an exploded view of the guide receptacle 400. The top support 404 of the receptacle 400 include a plurality of screw holes (414, 416), a top surface 418, and a body 408 having a pair of wings, each wing extending down and angularly away from the top surface 418 and end to form two bottom surfaces (420a, 420b). where the wings are separated by a gap G. The bracket 402 is removably assembled to the top surface 418 using a first set of tightening screws screwed through the screw holes 414. In particular embodiments, the magnetic regions (406a, 406b) are assembled to the bottom surfaces (420a, 420b) of the top support 404 through a second set of tightening screws screwed through the screw holes 416. In specific inventive embodiments, the magnetic regions (406a, 406b) each include a receptacle chamber (422a, 422b) that house one or more magnets (700a, 700b) therein to produce the magnetic fields. The receptacle chambers (422a, 422b) may be removably assembled to the bottom surfaces (420a, 420b) of the top support 404 to allow a user to exchange the magnet(s) (700a, 700b) inside the receptacle chambers (422a, 422b) so as to adjust the magnetic attraction forces, or to allow the user to disinfect any components within the receptacle chambers (422a, 422b). It should be appreciated however that the receptacle chambers (422a, 422b) may be permanently assembled to the top support 404 to prevent a user from tampering with one or more magnets (700a, 700b) housed inside in the receptacle chambers (422a, 422b).

Figure 2C:
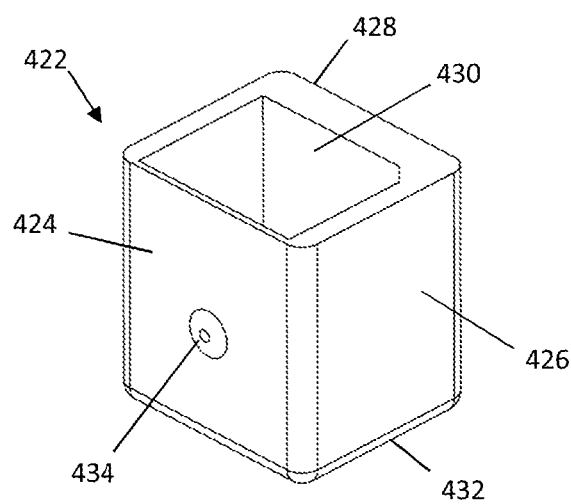
FIG. 2C is a perspective view of a receptacle chamber associated with the guide receptacle in accordance with embodiments of the invention.

Referring to FIG. 2C, the receptacle chamber 422 is shown in greater detail. In particular embodiments, the receptacle chamber(s) 422 includes an interface wall 424, at least two side walls 426, a back wall 428, an opening 430, a bottom wall 432, and a protrusion 434 positioned on the front interface wall 424. In one embodiment, the opening 430 of the receptacle chamber(s) 422 houses one or more magnets 700. In other embodiments, one or more of the walls of the chamber 422, such as the interface wall 424, is made of magnetic material to eliminate the need for a magnet 700 to be housed within the opening 430. In a particular embodiment, the magnetic region(s) (406a, 406b) do not include the chamber(s) (422a, 422b) but is rather made of a solid or semi-solid magnetic material as described above.

Figure 4B:
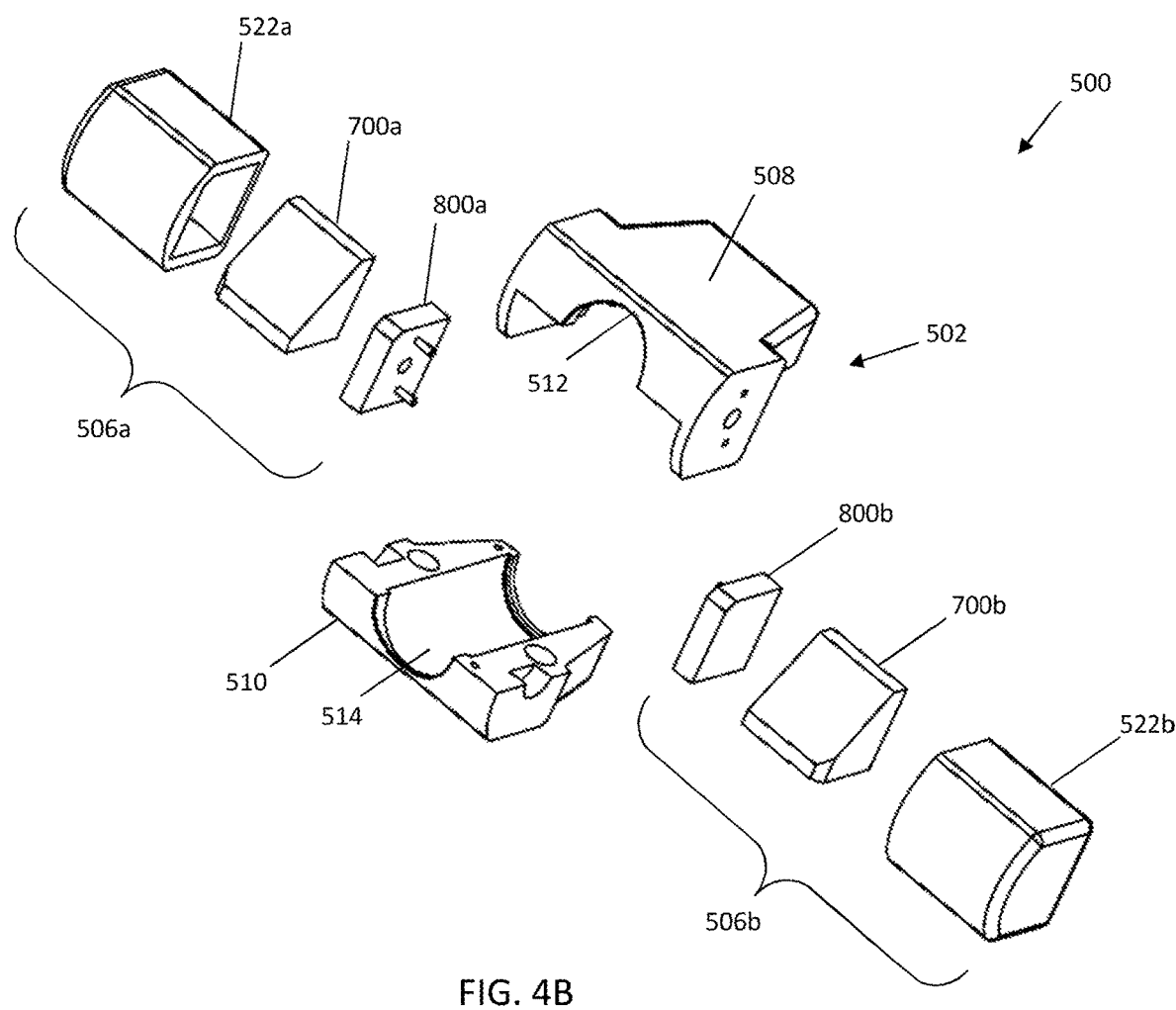
FIG. 4B depicts an exploded view of an impactor guide in accordance with embodiments of the invention.
Figure 4C:
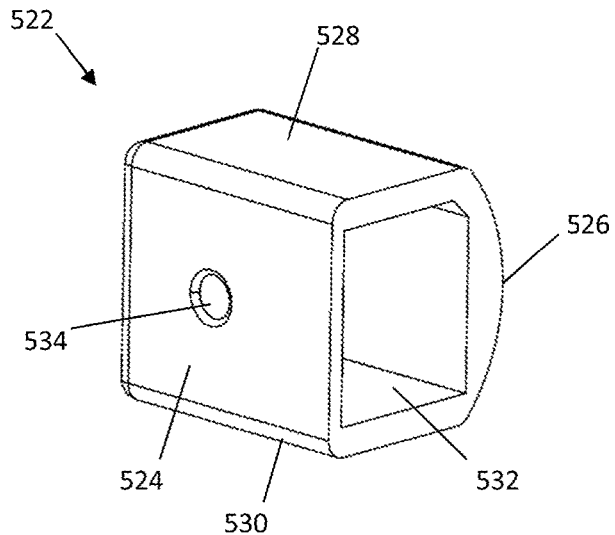
FIG. 4C depicts a guide chamber associated with the impactor guide in accordance with embodiments of the invention.

The protrusion 434 on the interface wall 424 of the receptacle chamber(s) (422a, 422b) engages with an indentation 534 (as shown in FIG. 4C) associated with the impactor guide 100 such that the guide receptacle 400 and impactor guide 500 self-align to their original positions with respect to each other following an off-axis impaction force. This self-alignment ensures the impactor 300 re-aligns to the planned POSE when the guide receptacle 400 and impactor guide 500 re-couple following an off-axis impaction force. The protrusion 434 and indentation 534 also increase the magnetic surface area and consequently increase the magnetic forces between the guide receptacle 400 and the impactor guide 500.

Figure 2D:
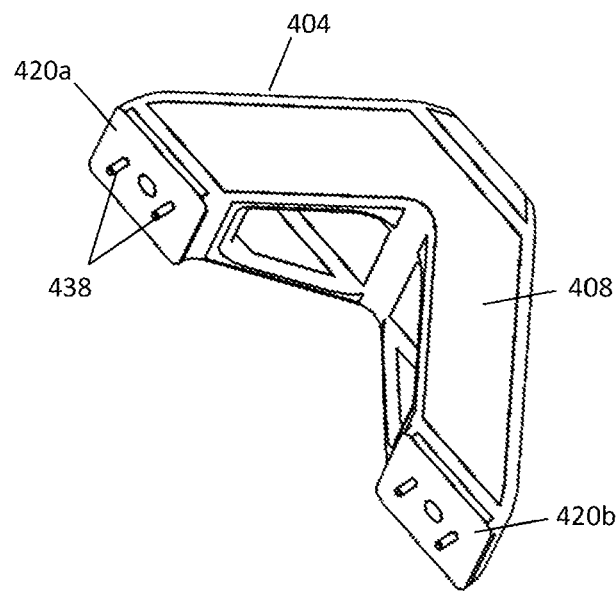
FIG. 2D is a perspective view of a top support of the guide receptacle in accordance with embodiments of the invention.
Figure 3:
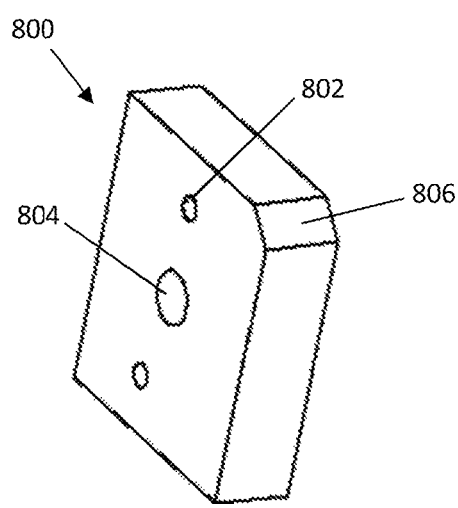
FIG. 3 depicts a lid for a receptacle chamber or guide chamber in accordance with embodiments of the invention.

In a specific embodiment, with reference to FIGS. 2B, 2D, and particularly FIG. 3, the opening 430 of the receptacle chamber(s) (422a, 422b) are covered by lid(s) (800a, 800b) to seal and protect the magnet(s) (700a, 700b) housed inside the receptacle chamber(s) (422a, 422b). A permanent connection, such as a laser weld, between the lid 800 and the receptacle chambers (422a, 422b) ensures the chambers (422a, 422b) are leak proof such that biological fluids cannot enter the chambers (422a, 422b). The lid 800 may further include a plurality of alignment holes 802 and at least one screw hole 804. The receptacle chamber(s) (422a, 422b) are therefore assembled to the guide receptacle 400 using a second set of tightening screws screwed through the screw holes 416 and 804. The alignment holes 802 may further receive alignment pins 438 projecting from the bottom surfaces (420a, 420b) of the top support 404 to further stabilize the chambers (422a, 422b) to the top support 404 and to ensure the chambers (422a, 422b) are accurately assembled in the correct POSE to the guide receptacle 400. This accuracy and stability, and the accuracy and stability of all the components assembled in the impactor assembly 100 are important because it directly affects how well the impactor 300 gets aligned in the planned POSE to impact the prosthesis 330. In particular, the alignment of the cup prosthesis in the acetabulum is directly correlated with patient outcomes and implant longevity.

With reference to FIG. 4A, a particular embodiment of the magnetic impactor guide 500 is shown. The magnetic impactor guide 500 may include a frame 502 and one or more guide magnetic regions 506 assembled laterally to the frame 502. In a specific embodiment, the impactor guide 500 includes two guide magnetic regions (506a, 506b) spaced a distance apart to complement the receptacle magnetic regions (406a, 406b) of the guide receptacle 400. As described above, the one or more guide magnetic regions (506a, 506b) magnetically couple with one or more receptacle magnetic regions (406a, 406b) to form the magnetic interface MI. The frame 502 includes an opening 504 to support and guide the impactor 300 therewithin. The opening 504 allows the impactor 300 to translate along the impaction axis 310 and rotate about the impaction axis 310, while constraining movement in all of the remaining degrees-of-freedom. In a specific embodiment, the frame 502 may further include a projection 512. The projection 512 may be a part of the shape of the frame 502 or an added component thereto. The projection 512 may have a width (constant or variable) that is equal to or less than the distance of the gap G of the guide receptacle 400 such that the projection 512 may fit between the two receptacle magnetic regions (406a, 406b). Therefore, the projection 512 may further stabilize and align the impactor guide 500 with the guide receptacle 400 when the two are magnetically coupled.

With reference to FIG. 4B, particular embodiments of the components associated with the impactor guide 500 are shown in an exploded view. The frame 502 may include a first portion 508 having a first channel 512, and a second portion 510 having an opposing channel 514, that assemble to form the opening 504. In a particular embodiment, a user, or manufacturing technician may decouple the first portion 508 from the second portion 510 to install the impactor 300 to the impactor guide 500 prior to a surgical procedure. In other embodiments, the impactor 300 is pre-assembled to the impactor guide 500 and sterilizable as a single unit for use in multiple procedures. While at least one exemplary embodiment has been presented in the foregoing detailed description, it should be appreciated that the impactor guide 500 can accommodate a vast number of impactors with different shapes and sizes.

Figure 5:
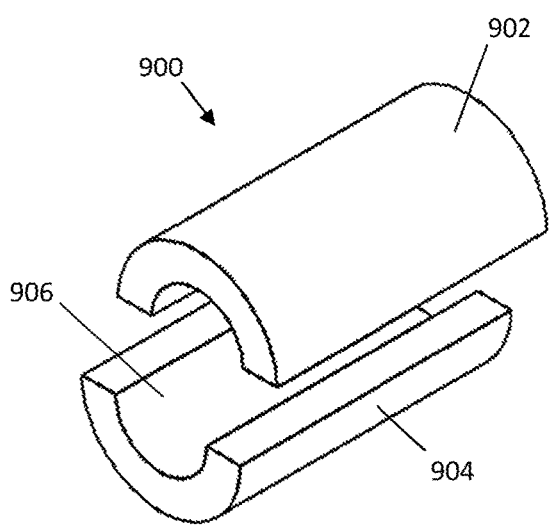
FIG. 5 depicts a bearing sleeve in accordance with embodiments of the invention.

Referring to FIG. 5, the impactor guide 500 may include a bearing sleeve 900 situated inside the opening 504 of the frame 502. The bearing sleeve 900 further having a first part 902 and a second part 904 that join together to form a bearing opening 906. The bearing opening 906 may accommodate the impactor 300. In a particular embodiment, the bearing sleeve 900 provides a smooth surface for the rotation and translation of the impactor 300 inside the impactor guide 500. The bearing sleeve 900 may further include a plurality of ball bearings. It should be appreciated that the bearing sleeve 900 may be in any shape, size or material. Also, the scope of the present invention does not require the use of bearing sleeve to be present or used when present, nor is the scope limited to these components.

In a specific embodiment, with reference back to FIG. 4B, the guide magnetic regions (506a, 506b) include guide chambers (522a, 522b) that house one or more magnets (700a, 700b) therewithin to produce the magnetic field. The guide chambers (522a, 522b) magnetically couple with the receptacle chambers (422a, 422b) to form the magnetic interface MI. The guide chambers (522a, 522b) may directly assemble, either removably or permanently, to the frame 502 via fastening elements, such as screws.

In a particular embodiment, referring to FIG. 4C, the guide chamber(s) (522a, 522b), includes a back interface wall 524, a front wall 526, a top wall 528, a bottom wall 530, an opening 532, and an indentation 534 on the surface of the back interface wall 524. The opening 532 may house the magnets 700 similar to the receptacle chambers (422a, 422b) associated with the guide receptacle 400. In other embodiments, the back interface wall 524 may be made of magnetic material alleviating the need for a magnet to be housed within the opening 532. In another embodiment, the guide magnetic regions (506a, 506b) do not include guide chambers (522a, 522b) but instead are at least partially made of a solid or semi-solid magnetic material.

The opening 532 of the guide chambers (522a, 522b) may further be covered and assembled to the frame 502 by lids (800a, 800b) in a similar fashion as described above with respect to the receptacle chamber 422 and lid 800 assembly to the top support 404 of the guide receptacle 400.

The indentation 534 associated with the guide chambers (522a, 522b) engage with the protrusions (434a, 434b) of the receptacle chambers (422a, 422b) to self-align the impactor guide 500 and the guide receptacle 400 in their original positions as the impactor guide 500 and the guide receptacle 400 re-couple following an off-axis impaction force. In a specific embodiment, the indentation 534 and protrusion 434 are hemi-spherically shaped such that the indentation 534 and protrusion 434 easily slide into one another during the re-coupling. It should be appreciated however that the indentation 534 and protrusion 434 may be of any shape or size. In a specific embodiment, additional indentations 534 and protrusions 434 are added to the back interface wall 534 and front interface wall 424, respectively, to increase the accuracy of alignment as well as the contact surface area to increase the magnetic attraction force.

Although this particular embodiment is not limited to this design, a front outer surface of the guide magnetic regions (506a, 506b) have a differently shaped front outer surface of the receptacle magnetic regions (406a, 406b). For example, the front walls (526a, 526b) of the guide chambers (522a, 522b) may have a curved outer surface, and the front interface walls (424a, 424b) of the receptacle chambers (422a, 422b) may have a flat outer surface. Therefore, a user cannot inadvertently couple the curved front walls (526a, 526b) of the guide chambers (522a, 522b) to the flat front interface wall 424 of the receptacle chambers (422a, 422b). This is important if the shape of the magnets 700 are not symmetric and/or the magnets 700 associated with the guide chamber 522 and receptacle chamber 422 need to align in a specific configuration as further described below.

Figure 6:
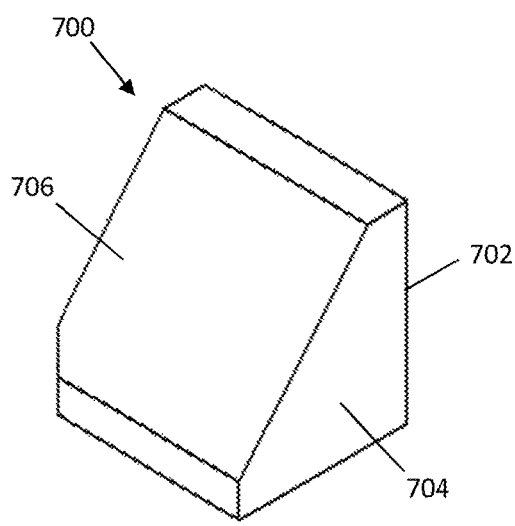
FIG. 6 depicts a magnet in accordance with embodiments of the invention.

Referring to FIG. 6, a specific embodiment of a magnet 700 is shown. The magnets (700a, 700b) are adapted to be housed within the receptacle chambers (422a, 422b) and guide chambers (522a, 522b) to produce the magnetic attraction forces to form the magnetic interface MI. The magnet 700 generally includes a positive pole, a negative pole, an interface wall 702, at least two side walls 704, and a back wall 706. In specific embodiments, the back wall 706 of the magnet 700 is partially tapered such that magnet 700 varies in thickness along a length of the magnet 700. Therefore, the magnet 700 has a gradient of magnetic forces dependent on the thickness of the magnet 700.

Figure 7:
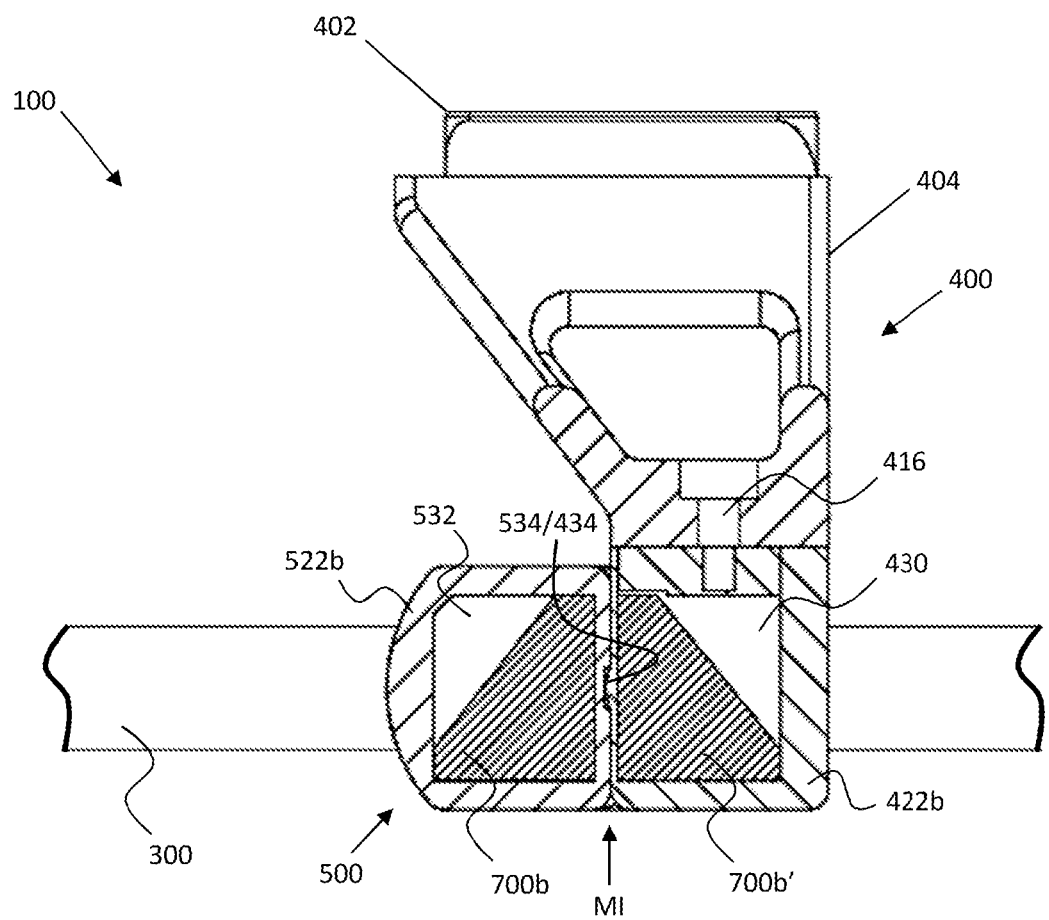
FIG. 7 depicts a partial cross sectioned view of the guide receptacle joined to the impactor guide in accordance with embodiments of the invention.

In a specific embodiment, with reference to FIG. 7, a first magnet 700b is housed in the guide chamber 522b of the impactor guide 500, where the interface wall 702b of the first magnet 700b is positioned adjacent to the back interface wall 524 on the inside of the guide chamber 522b. A second magnet 700b' is housed in the receptacle chamber 422b of the guide receptacle 400, where the interface wall 702b' of the second magnet 700b' is positioned adjacent to the front interface wall 424 on the inside of the receptacle chamber 422b. The interface walls (702b, 702b') of the magnets (700b, 700b') have opposing polarity to attract the impactor guide 500 to the guide receptacle 400 to form the magnetic interface MI. The receptacle chamber 422b and guide chamber 522b self-align to one another by way of the protrusion 434 mating with the indentation 534.

Figure 8:
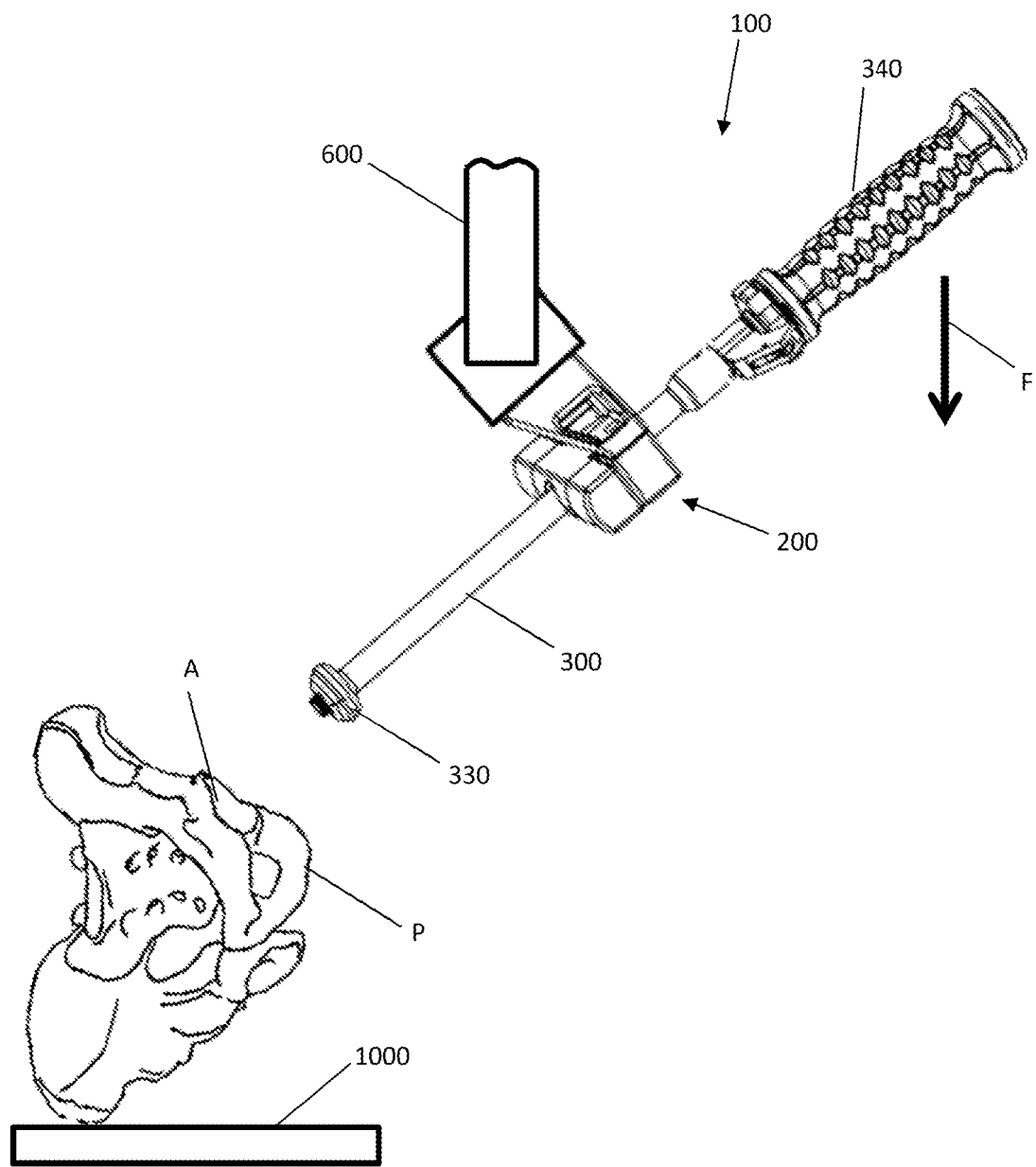
FIG. 8 depicts the magnetic impactor assembly positioned above an acetabulum of a subject.

In a particular embodiment, the first magnet 700b and second magnet 700b' are housed within the chambers (422b, 522b) such that the first magnet 700b mirrors the second magnet 700b'. In this arrangement, the interface wall 702b of the first magnet 700b has an opposing polarity than the interface wall 702b' of the second magnet 700b to create the attraction force therebetween. In addition, the tapering of the first back wall 706b of the first magnet 700b mirrors the tapering of the second back wall 706b' of the second magnet 700b' as shown in FIG. 7. This creates a gradient of attraction forces between the two magnets (700b, 700b') as the thickness of the magnets (700b, 700b') changes with the taper, where the greatest thickness and therefore the largest magnetic attraction is near the bottom walls (432, 530) of the coupler chambers (422b, 522b). This is particularly advantageous for a couple reasons. For one, with reference to FIG. 8, a patient's anatomy, such as a patient's pelvis P, is typically situated on a surgical table 1000 that lies below the impactor 300. The impactor 300 therefore approaches the acetabulum A from above and usually at an angle as depicted in FIG. 8. The impactor 300 may include a handle 340 that generates a large downward force F on the impactor 300, where the guide assembly 200 acts as a fulcrum. To counteract the downward force F, it is advantageous to have the largest attraction force near the bottom walls (432, 530) of the coupler chambers (422b, 522b). However, if the attraction force between the two magnets (700b, 700b') is too great, then the impactor guide 500 will not decouple from the guide receptacle 400 following an off-axis impaction force of a certain magnitude. Thus, there is a balancing act to have an attraction force that can sufficiently hold and guide the impactor 300 in a planned POSE, while still allowing the impactor 300 to decouple from surgical device, such as the electromechanical arm 600, if an off-axis impaction force of a certain magnitude occurs. Varying the thickness of the magnets (700b, 700b') by way of the taper is one such method for controlling/balancing these attraction forces. Other embodiments for controlling the attraction force include joining/disjoining two or more magnets, exchanging one or more of the magnets having a higher or lower magnetic field, and/or inducing a magnetic field to a particular strength by changing a current flowing around a magnetizable material.

In addition, in specific embodiments, the magnetic attraction force is chosen such that impactor guide 500 and the guide receptacle 400 in fact decouple when an off-axis impaction force occurs, but is strong enough to snap the guide 500 and the receptacle 400 immediately back together. Therefore, the user does not have to constantly re-assemble the guide assembly 200, but rather the assembly 200 immediately re-assembles from the attraction forces and self-aligns via the protrusion 434 and indentation 534.

Figure 9:
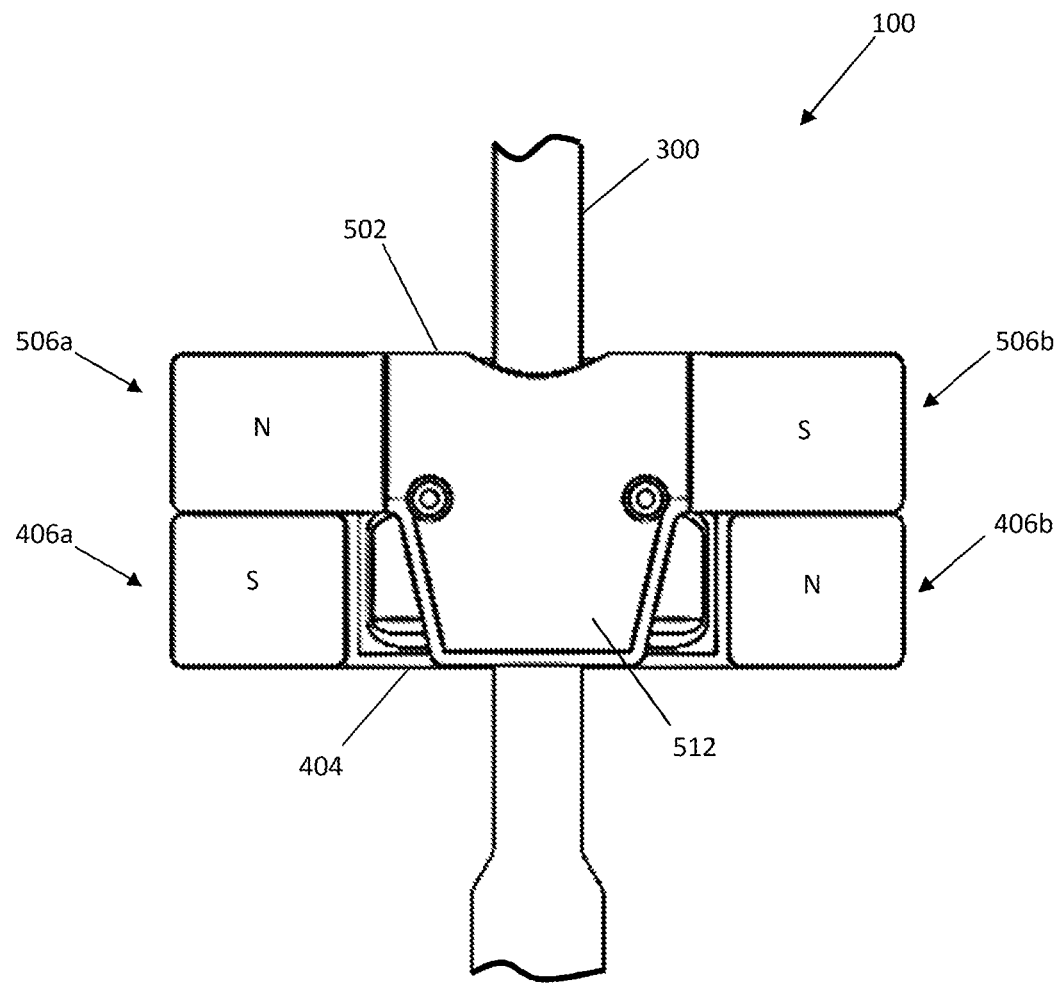
FIG. 9 depicts a bottom view of the impactor assembly in accordance with embodiments of the invention.

With reference to FIG. 9, a bottom view of the impactor assembly 100 is shown. In a specific embodiment, where the impactor guide 500 includes two guide magnetic regions (506a, 506) and the guide receptacle 400 includes two receptacle magnetic regions (406a, 406b), there is the possibility that the impactor guide 500 can be inversely assembled to the guide receptacle 400. In addition, if the magnetic regions (406a, 406b, 506a, 506b) include chambers (422a, 422b, 522a, 522b) housing magnets 700 that need to align in a particular configuration (e.g., the mirroring of the magnets (700b, 700b') as shown in FIG. 7), then inversely assembling the impactor guide 500 to the guide receptacle 400 creates an inverse alignment configuration between the two magnets (400a, 400b). For example, with reference to FIG. 7, if the impactor guide 500 was inversely assembled to the guide receptacle 400, where guide chamber 522a would align with receptacle chamber 422b, then the magnets no longer mirror each other. Rather, the thickest portion of the first magnet 700b would align and attract with the thinnest portion of the second magnet 700b'.

To alleviate this problem, the polarity arrangement between the magnetic regions (406a, 506a) located on a first side of the guide assembly 200 is opposite of the polarity arrangement between the magnetic regions (406b, 506b) located on a second side of the guide assembly 200. This is shown in FIG. 9, where 'N' denotes a northern polarity closest to the magnetic interface MI, and 'S' denotes a southern polarity closest to the magnetic interface MI. Therefore, if a user were to try and inversely assemble the impactor guide 500 to the guide receptacle 400, the 'S' guide magnetic region 506b repels the 'S' receptacle magnetic region 406a.

While at least one exemplary embodiment has been presented in the foregoing detailed description, it should be appreciated that the magnet 700 may be any of known permanent, temporary or electromagnet but is preferably a permanent magnet. For example, the permanent magnet may include Neodymium Iron Boron (NdFeB or NIB), Samarium Cobalt (SmCo), Alnico and Ceramic or Ferrite. In a particular embodiment, the magnet 700 is a permanent magnet and more specifically is a Neodymium Iron Boron (NdFeB) magnet due to its high-strength. Also, embodiments of the magnet 700 may be in any shape or size. For instance, embodiments of the magnet 700 may be made into round bars, rectangular bars, horseshoes, rings or donuts, disks, rectangles, multi-fingered rings, paint, powder or mold. The magnet 700 may also be magnetized where negative and positive poles are based on the usage and configuration of the magnet. Additionally, the magnetization of a particular material may be done by any method known by the person of skill in the art.

Slap-Hammer

Figure 10:
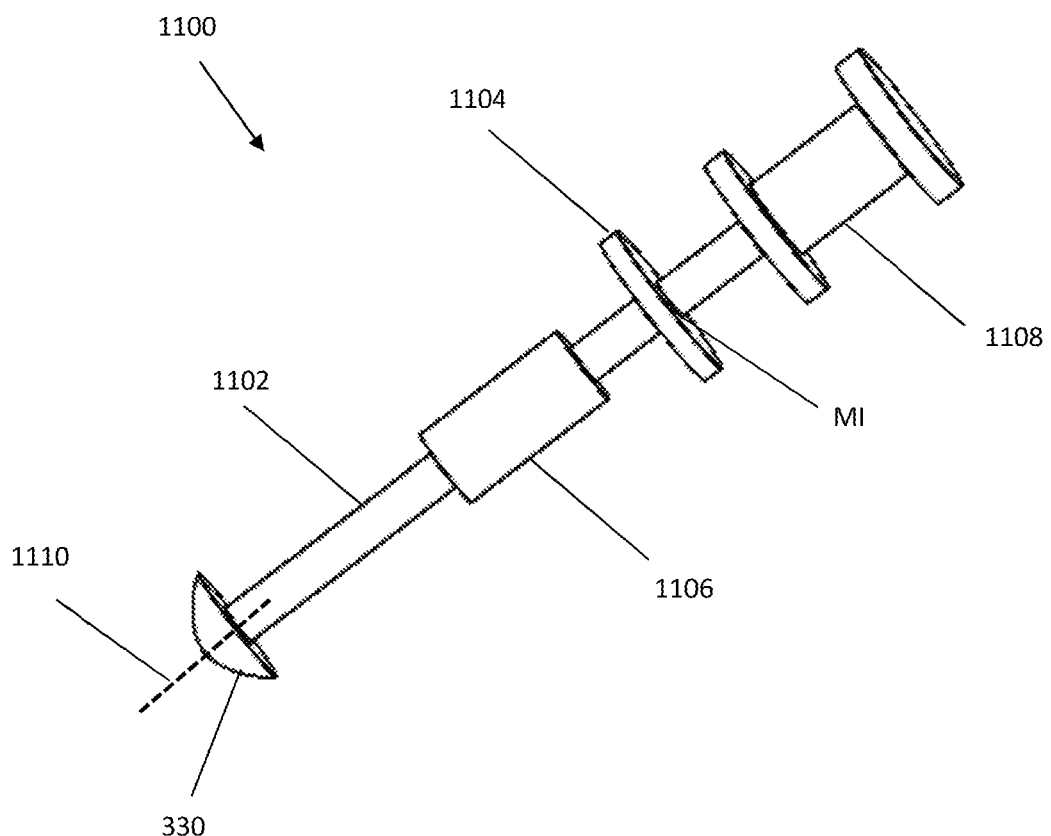
FIG. 10 depicts a slap hammer in accordance with embodiments of the invention.

To control an amount of force while removing a prosthesis from a bone, embodiments of an inventive slap hammer having a magnetic compliant interface is shown in FIG. 10. The slap hammer 1100 includes an impactor guide 1102, a guide receptacle 1104 and an impactor 1106. The impactor guide 1102 includes a shaft having a first end, a second end, and a magnetic shaft portion between the first end and second end. The first end may include an attachment mechanism for assembling a prosthesis 330 thereto. The second end may include a handle 1104. The impactor 1106 is a weight that is slidable along the length of the shaft in the direction of an impaction axis 1110. The guide receptacle 1104 may be a plate or other body having an impaction surface that receives forces from the impactor 1106, and a magnetic surface that contacts a portion of the shaft. The magnetic surface of the guide receptacle magnetically couples with the magnetic shaft portion to form a magnetic interface MI. The magnetic attraction forces between the magnetic surface and magnetic shaft portion may be chosen (i.e. threshold amount of force) such that when the impactor 1106 applies a certain amount of force on the guide receptacle 1104, the guide receptacle 1104 breaks from the magnetic interface MI to reduce the transmission of excessive forces on a patient during the removal of the prosthesis 330 from the patient. The threshold amount of force may be chosen so as to break the magnetic interface MI before patient harm occurs.

Other Embodiments

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.

The invention claimed is:

1. A guide assembly for an impactor, comprising:
an impactor guide having a guide magnetic region and an opening having an opening axis, wherein the opening constrains movement of the impactor to translation along the opening axis of the opening;
a guide receptacle having a receptacle magnetic region for receiving the guide magnetic region to form a magnetic interface between the receptacle magnetic region and the guide magnetic region to locate the opening axis along a first axis and having a magnetic attraction force sufficient to hold the impactor guide to the guide receptacle when translation of the impactor is substantially along the first axis and insufficient to hold the impactor guide to the guide receptacle when an impaction force greater than a predetermined threshold is applied to the impactor along a second axis that is not substantially parallel to the first axis.

2. The guide assembly of claim 1, wherein the receptacle magnetic region comprises a receptacle chamber housing a receptacle magnet, and the guide magnetic region comprises a guide chamber housing a guide magnet.

3. The guide assembly of claim 2, wherein the receptacle magnet and the guide magnet are selected from a permanent magnet, a temporary magnet, or an electromagnet.

4. The guide assembly of claim 2, wherein the receptacle magnet and the guide magnet are permanent magnets.

5. The guide assembly of claim 2, wherein the receptacle magnet and the guide magnet are both shaped with a varying thickness to create a gradient of magnetic forces dependent on the thickness, and wherein the shape of the receptacle magnet substantially mirrors the shape of the guide magnet when the impactor guide and guide receptacle are magnetically coupled.

6. The guide assembly of claim 1, wherein the receptacle magnetic region and the guide magnetic region are one of: a) a body made of a solid magnetic material; b) a body partially made of a solid magnetic material; or c) a body having a coating of magnetic material.

7. The guide assembly of claim 1, wherein the guide receptacle further comprises a bracket, wherein the bracket is configured to couple the guide receptacle to a surgical device or instrument.

8. The guide assembly of claim 7, wherein the surgical device is a robotic surgical system.

9. The guide assembly of claim 1, wherein the receptacle magnetic region further comprises a protrusion and the guide magnetic region further comprises an indentation, wherein the protrusion and the indentation are configured to self-align when the impactor guide is magnetically coupled to the guide receptacle.

10. The guide assembly of claim 1 wherein the impactor guide further comprises a second guide magnetic region; and wherein the guide receptacle further comprises a second receptacle magnetic region, wherein the receptacle magnetic region and the second receptacle magnetic region are configured to magnetically couple with the guide magnetic region and the second guide magnetic region, respectively, to form the magnetic interface.

11. The guide assembly of claim 10 wherein the guide magnetic region and the receptacle magnetic region have a first polarity arrangement and the second guide magnetic region and the second receptacle magnetic region have a second polarity arrangement, wherein the first polarity arrangement is opposite to the second polarity arrangement.

12. The guide assembly of claim 10 wherein the guide magnetic region and the second guide magnetic region are separated by a gap.

13. The guide assembly of claim 12 wherein the gap comprises a third axis coincident with the first axis of the opening when the receptacle magnetic region and the guide magnetic region are magnetically coupled, and wherein the first axis of the opening breaks coincidence with the third axis when the magnetic interface decouples.

14. The guide assembly of claim 1 further comprising a second guide magnetic region, wherein the guide magnetic region comprises a first magnet and the second guide magnetic region comprises a second magnet.

15. The guide assembly of claim 1 further comprising a bearing sleeve formed as an insert in the impactor guide and defining walls of the opening.

16. The guide assembly of claim 15 wherein the bearing sleeve is formed from a plurality of parts.

17. The guide assembly of claim 1 wherein the magnetic interface is formed by permanent magnets each independently formed of Neodymium Iron Boron (NdFeB or NIB), Samarium Cobalt (SmCo), or Alnico.

* * * * *